(12) United States Patent
Xu

(10) Patent No.: US 11,713,329 B2
(45) Date of Patent: Aug. 1, 2023

(54) INTERMEDIATES USEFUL IN THE PREPARATION OF HALICHONDRIN COMPOUNDS AND METHODS FOR PREPARING THE SAME

(71) Applicant: BEIJING TIENYI LUFU PHARMATECH CO. LTD., Beijing (CN)

(72) Inventor: Weiping Xu, Beijing (CN)

(73) Assignee: BEIJING TIENYI LUFU PHARMATECH CO. LTD., Beijing (CN)

( * ) Notice: Subject to any disclaimer, the term of this patent is extended or adjusted under 35 U.S.C. 154(b) by 303 days.

(21) Appl. No.: 16/768,943

(22) PCT Filed: Nov. 7, 2019

(86) PCT No.: PCT/CN2019/116349
§ 371 (c)(1),
(2) Date: Jun. 2, 2020

(87) PCT Pub. No.: WO2020/119345
PCT Pub. Date: Jun. 18, 2020

(65) Prior Publication Data
US 2021/0163509 A1    Jun. 3, 2021

(30) Foreign Application Priority Data
Dec. 10, 2018 (CN) .......................... 201811508481.1

(51) Int. Cl.
*C07D 263/26* (2006.01)
*C07F 7/08* (2006.01)
*C07D 277/16* (2006.01)
*C07D 493/22* (2006.01)
*C07F 7/18* (2006.01)

(52) U.S. Cl.
CPC .......... *C07F 7/0812* (2013.01); *C07D 263/26* (2013.01); *C07D 277/16* (2013.01); *C07D 493/22* (2013.01); *C07F 7/1892* (2013.01)

(58) Field of Classification Search
CPC .................................................. C07D 263/26
See application file for complete search history.

(56) References Cited

FOREIGN PATENT DOCUMENTS

WO    9317690 A1    9/1993
WO    2016003975 A1    1/2016

OTHER PUBLICATIONS

Ueda, Atsushi, et al. "Total Synthesis of Halichondrin A, the Missing Member in the Halichondrin Class of Natural Products." J. Am. Chem. Soc. (2014), vol. 136, pp. 5171-5176) (Year: 2014).*
American Chemical Society. Chemical Abstract Service. RN 160447-16-5. First entered into STN/made available to public on Jan. 27, 1995. (Year: 1995).*
Atsushi Ueda et al.; Total Synthesis of Halichondrin A, the Missing Member in the Halichondrin Class of Natural Products; Journal of the American Chemical Society; Mar. 17, 2014, 136, pp. 5171-5176.
Cheng-Guo Dong et al.; New Syntheses of E7389 C14-C35 and Halichondrin C14-C38 Building Blocks: Reductive Cyclization and Oxy-Michael Cyclization Approaches; Journal of the American Chemical Society; Oct. 6, 2009, 131, 15642-15646.
Cheng-Guo Dong et al.; Supporting Information, New Syntheses of E7389 C14-C35 and Halichondrin C14-C38 Building Blocks: Reductive Cyclization and Oxy-Michael Cyclization Approaches; S1-S40, published on http://pubs.acs.org, Oct. 6, 2009.
Zhigao Zhang et al.; Total Synthesis of ( )-Exiguolide; Organic Letters, Sep. 15, 2015, vol. 17, pp. 4706-4709.

* cited by examiner

*Primary Examiner* — John S Kenyon
(74) *Attorney, Agent, or Firm* — NKL Law; Allen Xue

(57) ABSTRACT

The invention relates to intermediates useful in the preparation of halichondrin compounds, methods for preparing the same and use thereof, such as halichondrins, eribulin, or their analogs. The intermediates, the methods and use thereof are used for the synthesis of the C20-C26 fragment of halichondrin compounds. The raw materials in the synthetic route of the invention are cheap and easily obtained, the sources and the qualities of the raw materials are reliable. The choice of the methods useful in the synthesis of chiral central structures are based on the structural characteristics of the reactants, thus effectively improving the synthesis efficiency, reducing the difficulties and risks of product quality control, and avoiding the use of highly toxic and expensive organotin catalysts to significantly decrease costs and improve environmental friendliness.

11 Claims, 1 Drawing Sheet

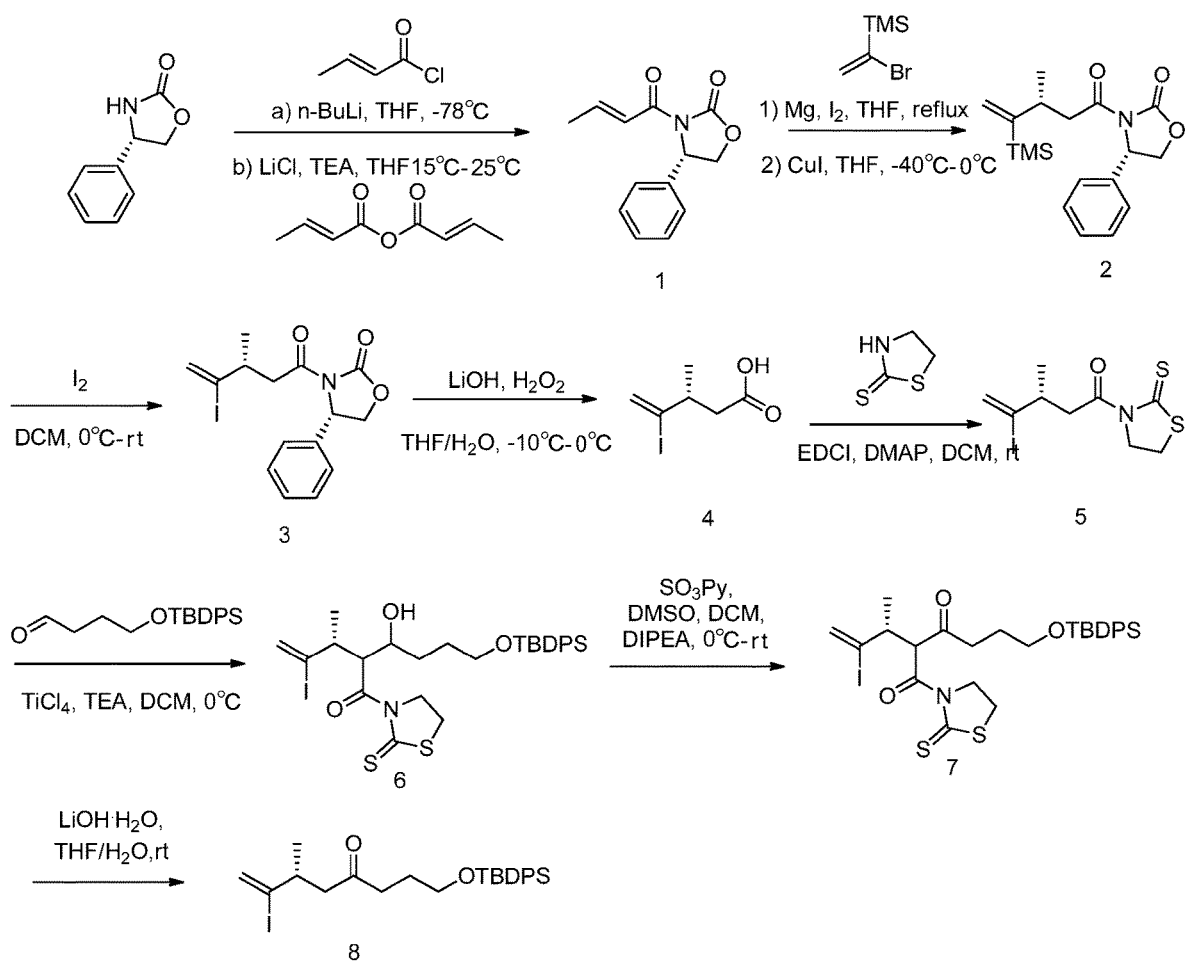

INTERMEDIATES USEFUL IN THE PREPARATION OF HALICHONDRIN COMPOUNDS AND METHODS FOR PREPARING THE SAME

CROSS-REFERENCE TO RELATED APPLICATIONS

This application is a National Stage of International Application No. PCT/CN2019/116349, filed Nov. 7, 2019, which claims the benefit of priority from Chinese Patent Application No. 201811508481.1, filed Dec. 10, 2018, which is entitled "Intermediates useful in the preparation of halichondrin compounds and methods for preparing the same," the content of which is incorporated herein by reference in its entirety.

TECHNICAL FIELD

The invention relates to intermediate compounds which can be used for the preparation of halichondrins or their analogs, particularly the intermediate compounds useful in the synthesis of eribulin, and relates to the methods for preparing these intermediate compounds, belonging to the technical field of organic synthesis.

BACKGROUND ART

Halichondrins (hereinafter referred to as HB) are present in marine sponges, having structures of polyether macrolide. Such substances have strong antitumor effects and broad application prospects of medicines. On the basis of the differences in structures, these natural products are classified into the following categories: norhalichondrin, halichondrin, homohalichondrin, etc., and each class has a series of representative subtypes. The subtypes and specific structures are known in the art and are disclosed in detail in WO2016003975A1, which is referred to as prior art in this paper; eribulin (hereinafter referred to as EB) is a structurally simplified analog of halichondrin, which has been currently used clinically to treat advanced breast cancer and liposarcoma.

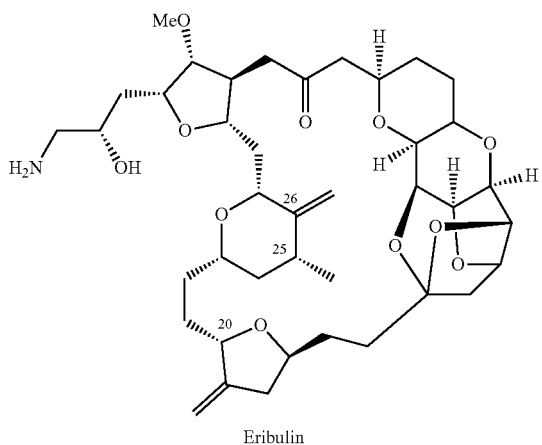 [SMILES: C=C1C[C@@H]2CCC34CC5O[C@H]6[C@@H](O3)[C@H]3O[C@H](CCC3O[C@H]6[C@H]5O4)CC(=O)C[C@@H]3[C@@H](OC)[C@@H](C[C@H](O)CN)O[C@H]3C[C@H]3O[C@@H](CC[C@@H]1O2)C[C@@H](C)C3=C]

Eribulin

HB and EB both can not be obtained from natural sources in large quantities, and can only obtained by artificial synthesis. Due to the similar structures of these compounds, and particularly the same structure of the C1-C29 fragment, suitable intermediate compounds can be used to synthesize these compounds. For example, the intermediates shown in Formula 1a and Formula 4 below can be used to synthesize the C20-C35 fragment of eribulin.

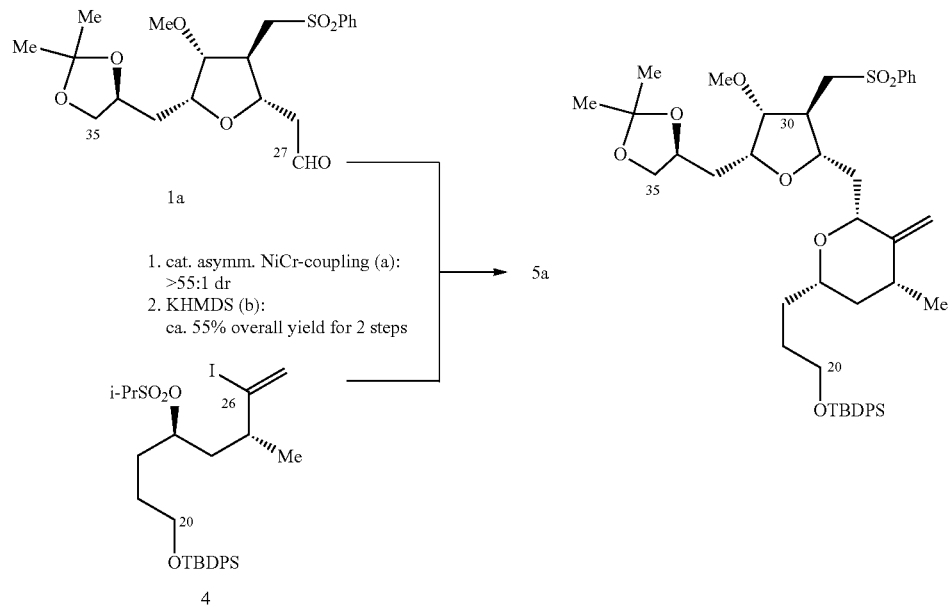

Alternately, the intermediates shown in Formula 1b and Formula 6 below can be used to synthesize the C20-C35 fragment of eribulin.

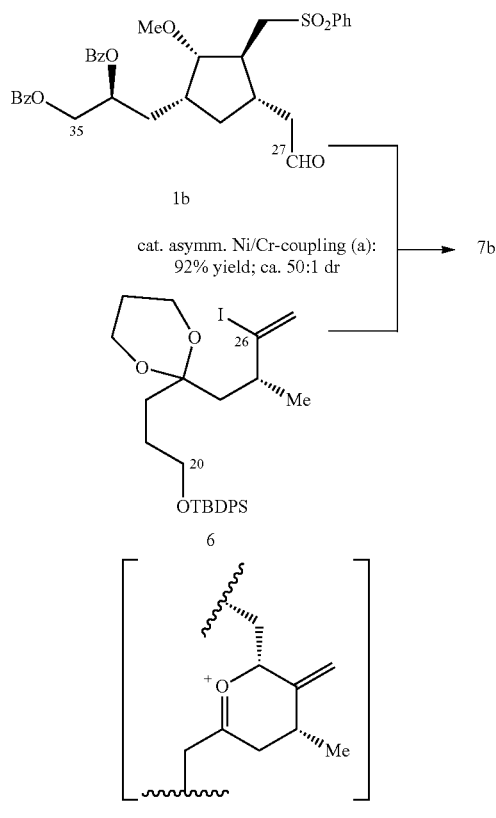
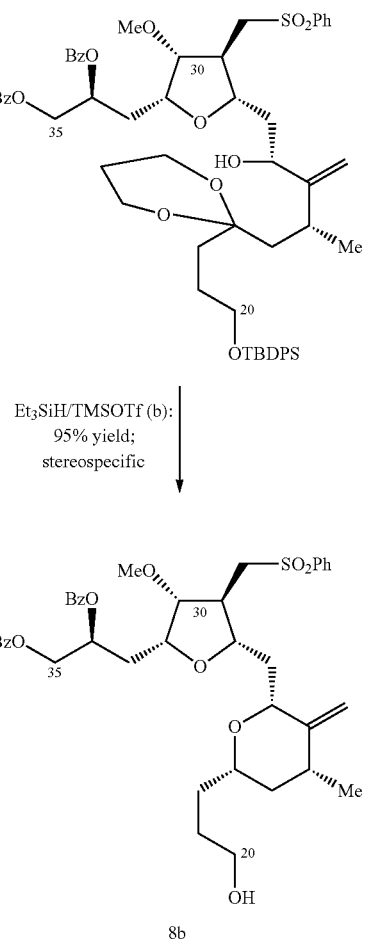

However, in the prior art, there are many disadvantages in the methods for preparing the compound of Formula 4 or the compound of Formula 6. For example, the synthetic routes are too long, it is difficult to control the optical purities of starting materials, the highly toxic and expensive n-Bu$_3$S$_n$H reagent is used, and the stereoselectivity is poor, etc. These disadvantages cause a series of problems in production such as cost control, environment and labor protection, product quality, etc. Therefore, in order to improve the methods for preparing halichondrin pharmaceutical compounds, there is an urgent need for the development of intermediates or synthetic methods to improve synthesis efficiency, reduce production cost, facilitate industrial large-scale production, increase selectivity, yield and purity, and to be environmentally friendly.

SUMMARY OF THE INVENTION

To solve the above problems, the invention provides the following intermediates useful in the synthesis of halichondrins and their analogs, and particularly the intermediates used for the synthesis of the C20-C26 fragment of eribulin and the methods of the preparation thereof.

The first aspect of the invention is to provide a method for preparing the compound of Formula (8), which is defined as follows:

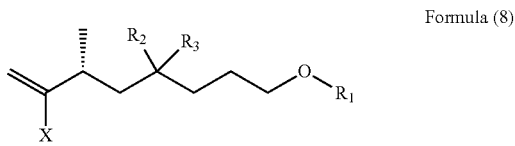

Formula (8)

wherein, $R_1$ is selected from hydroxyl protecting groups;

$R_2$ and $R_3$ are the same or different, and independently selected from H and $OR_a$, and $R_a$ is independently selected from the group consisting of H, $C_{1-10}$ alkyl, $R_bSO_2$, wherein $R_b$ is $C_{1-10}$ alkyl; or $R_2$ and $R_3$ both are $OR_a$, and two $R_a$ are bonded together to form $C_{1-6}$ alkylene; or $R_2$ and $R_3$ together with the carbon atom to which they are bonded form a carbonyl group;

X is selected from the group consisting of halogen, sulfonyloxy.

For example, $R_1$ is selected from the silyl hydroxyl protecting groups, such as TMS, TES, TBDMS, TBDPS, DIPS, DPS, TIPDS, etc.

For example, one of $R_2$ and $R_3$ is selected from H, the other is selected from $OR_a$, and $R_a$ is H or i-PrSO$_2$; or $R_2$ and $R_3$ both are $OR_a$, and two $R_a$ are bonded together to form n-propylidene; or $R_2$ and $R_3$ together with the carbon atom to which they are bonded form a carbonyl group;

for example, X is selected from the group consisting of chlorine, bromine, iodine, etc;

the method includes the following step:

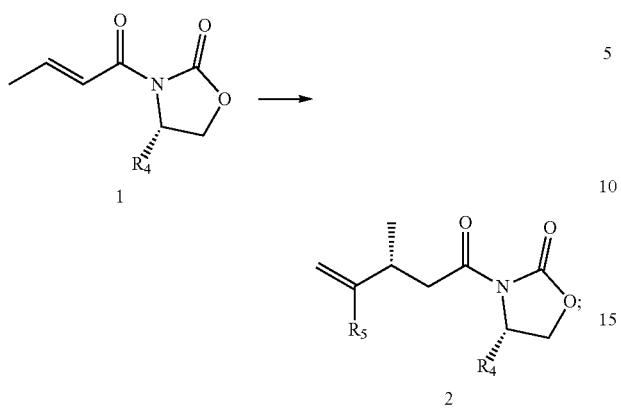

wherein, $R_5$ in Formula (2) is selected from silyl groups, e.g., TMS, TES, TBDMS, TBDPS, DIPS, DPS, TIPDS, etc.; the oxazolidinone moieties in Formula (1) and Formula (2) are oxazolidinone chiral auxiliary groups, for example, $R_4$ is $C_{1-10}$ alkyl, substituted or unsubstituted phenyl, or substituted or unsubstituted benzyl. Preferably, said $R_4$ is isopropyl, unsubstituted, monosubstituted or polysubstituted phenyl, or unsubstituted, monosubstituted or polysubstituted benzyl, in which the substituents are selected from the group consisting of hydroxy, nitro, dimethylamino.

Preferably, it also includes the step of recrystallizing the compound of Formula (2) once, twice or more times.

According to the invention, the compound of Formula (2) is obtained by reacting the compound of Formula (1) with a Grignard reagent $R_6MgX$ or $R_6Li$, in which $R_6$ is

According to the invention, the reaction is carried out in the presence of cuprous salts, such as cuprous chloride, cuprous bromide, cuprous iodide (CuI), cuprous cyanide, etc., in an inert atmosphere, at −50-0° C. and in a solvent. The solvent can be tetrahydrofuran or anhydrous diethyl ether, and the amount (mass) of the cuprous salt is about 10-25% of the reactant of Formula (1), preferably 15-20%.

According to the invention, after preparing the compound of Formula (2) from the compound of Formula (1), the content of optical isomers can be controlled and reduced by recrystallizing the compound of Formula (2). The solvent for the recrystallization is any solvent that can dissolve the compound of Formula (2) at room temperature or at a temperature which is slightly higher than room temperature, and can be for crystallization at a lower temperature (e.g., −10 to −30° C.), such as a non-polar organic solvent, preferably alkanes, for example, n-pentane, n-hexane, n-heptane, isooctane, or a mixed solvent thereof, such as petroleum ether.

Preferably, the recrystallization can be repeated multiple times. After one recrystallization, the isomer content of the compound of Formula (2) of the invention can be controlled to 1% or less, the isomer content after two recrystallizations can be controlled to 1% or less, and after multiple recrystallizations, the isomer content can be controlled in a lower range. It can be understood by those skilled in the art that the configuration of the chiral carbon atom to which the β-methyl group is connected in Formula (2) of the invention does not change in the subsequent conversion process, so the purity associated with the configuration of the chiral carbon atom is maintained.

According to the invention, the method for preparing the Grignard reagent includes the following steps:

Vinylsilanes

and a halogenated reagent are mixed at a relatively low temperature (e.g., −30 to −10° C.), an acid binding agent is added at room temperature, and then the mixture is refluxed to obtain a halogenated vinylsilane. The acid binding agent can be an organic or inorganic weak base, such as diethylamine, ethylenediamine, triethylamine, diisopropylamine, pyridine, potassium carbonate, sodium carbonate, cesium carbonate, etc.

The halogenated vinylsilane reacts with metallic magnesium or metallic lithium in an aprotic solvent to produce the corresponding Grignard reagent or lithium reagent. The aprotic solvent can be an ether solvent, e.g., diethyl ether, diisopropyl ether, tert-butyl methyl ether, cyclohexyl methyl ether, tetrahydrofuran, dioxane, etc., or a hydrocarbon solvent, such as n-pentane, n-hexane, n-heptane, benzene, toluene, xylene, etc.

Alternatively, the above-mentioned halogenated vinylsilane may also react with other easily obtained Grignard reagent in the above solvent, such as a methyl Grignard reagent, an ethyl Grignard reagent, a n-propyl Grignard reagent, an isopropyl Grignard reagent, etc., or an alkyllithium reagent easily obtained, such as methyl lithium, n-butyl lithium, sec-butyl lithium, tert-butyl lithium, to produce the corresponding Grignard reagent or lithium reagent through metal-halogen exchange reaction.

According to the method for preparing the compound of Formula (8) of the invention, it further includes the following reaction step of preparing the compound of Formula (3) from the compound of Formula (2):

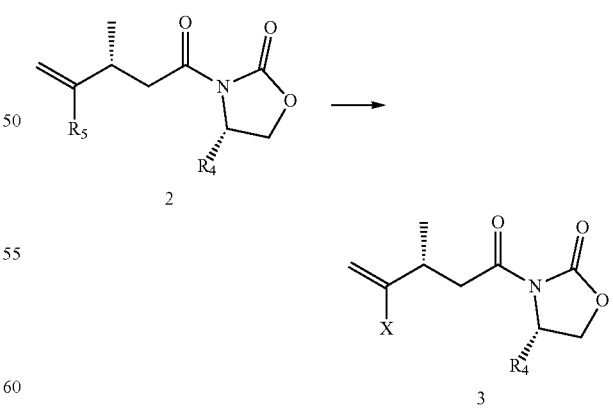

wherein, X in Formula (3) is halogen or a sulfonyloxy group.

According to the invention, the halogenation reaction is known to those skilled in the art, which is carried out in a suitable solvent at a mild reaction temperature, such as from 0° C. to room temperature. The halogenated reagent used can be $X_2$, $RCO_2X$, $R_nSiX_{4-n}$, wherein X is halogen of the group consisting of chlorine, bromine and iodine, and two X in $X_2$ may be different, R is selected from $C_{1-10}$ alkyl or fluorinated $C_{1-10}$ alkyl, and n is an integer of 1-3. Examples of the halogenated reagent can be elemental chlorine, elemental bromine, elemental iodine, BrCl, ICl, TMSCl, TMSI, $CF_3CO_2I$, etc.

Alternatively, the method for the preparation of the invention further includes converting a compound of Formula (3) with X as halogen into a compound of Formula (3) with X as a sulfonyloxy group according to the known substitution reaction in the art.

According to the method for preparing the compound of Formula (8) of the invention, it further includes the following step:

preparing the compound of Formula (1) from an oxazolidinone chiral auxiliary and the corresponding acyl compound

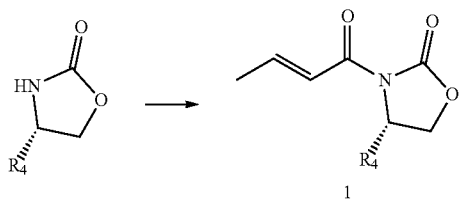

According to the invention, the reaction is performed under basic and low temperature conditions (−80° C. to −20° C.), and the catalytic amount of lithium chloride and the solvent used in the reaction are selectable. The base is selected from organic bases, inorganic bases or mixtures thereof, such as one or more of potassium carbonate, sodium carbonate, potassium bicarbonate, sodium bicarbonate, sodium hydroxide, potassium hydroxide, cesium carbonate, triethylamine, pyridine, piperidine, n-butyl lithium (n-BuLi). The solvent is, for example, tetrahydrofuran, N,N-dimethylformamide (DMF), dichloroethane, ethyl ether, carbon tetrachloride, or toluene, etc.; the acyl compound can be an ester, a carboxylic acid, an acyl halide, or an acid anhydride. In an embodiment of the invention, the oxazolidinone chiral auxiliary reacts with an acyl halide at −80 to −60° C., by using tetrahydrofuran as a solvent, under argon protection and in the presence of n-butyl lithium, and the mass amount of n-butyl lithium is about 30-50% of oxazolidinone; or the oxazolidinone chiral auxiliary reacts with an acid anhydride at −30 to −20° C., by using tetrahydrofuran as a solvent, in the presence of lithium chloride and triethylamine, and the mass amount of lithium chloride is about 35-55% of oxazolidinone.

According to the method for preparing the compound of Formula (8) of the invention, it further includes the following step: preparing the compound of Formula (4) from the compound of Formula (3):

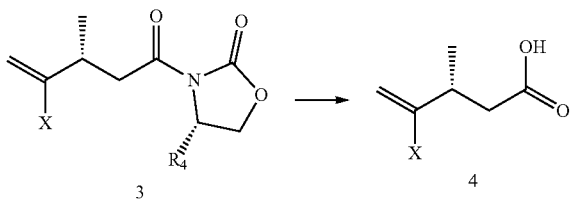

The reaction is performed under such conditions as to remove and separate the oxazolidinone chiral auxiliary, preferably the oxazolidinone chiral auxiliary being hydrolytically removed under basic conditions.

According to the invention, the reaction is carried out at −15 to 5° C., under basic conditions and in a solvent medium, and optionally in hydrogen peroxide. The reaction temperature can be −10 to 0° C., preferably −5 to 0° C. The base can be selected from organic bases, inorganic bases or mixtures thereof, such as one or more of potassium carbonate, sodium carbonate, potassium bicarbonate, sodium bicarbonate, cesium carbonate, lithium hydroxide, lithium hydroxide hydrate, sodium hydroxide, potassium hydroxide, calcium hydroxide, ammonia, sodium acetate, triethylamine, pyridine or piperidine. The solvent is a mixture of water and one or more of alcohols, ethers such as THF or dioxane, and acetone. The ratio (volume ratio) of water to the organic solvents in the mixture can be about 1:1 to 1:6, preferably about 1:2 to 1:3. As an embodiment of the invention, the reaction is carried out at −5 to 0° C., in a mixed solvent of tetrahydrofuran and water, in the presence of lithium hydroxide monohydrate and hydrogen peroxide, and the mass ratio of the compound of Formula (3) to hydrogen peroxide to lithium hydroxide monohydrate is 12-20:3-9:1-6.

According to the method for preparing the compound of Formula (8) of the invention, it further includes the following step: preparing the compound of Formula (5) from the compound of Formula (4):

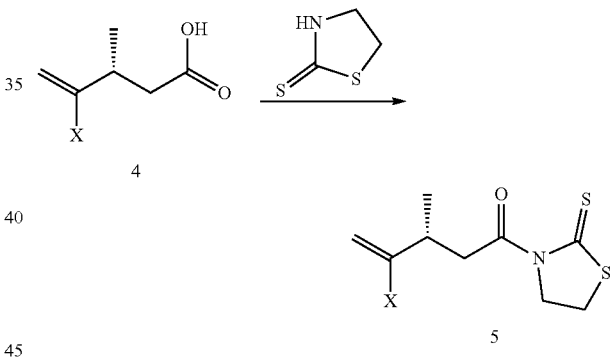

According to the invention, the reaction is carried out in the presence of coupling agents, which can be EDCI/DMAP, EDC/DMAP, EDC/NHS, or DCC/NHS system, and at 15 to 40° C., preferably at room temperature (20 to 25° C.). The solvent used in the reaction can be dichloromethane (DCM), tetrahydrofuran (THF), dimethylformamide (DMF), etc.

According to the method for preparing the compound of Formula (8) of the invention, it further includes the following step: preparing the compound of Formula (6) from the compound of Formula (5) and an aldehyde:

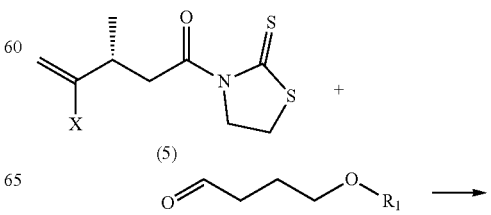

-continued

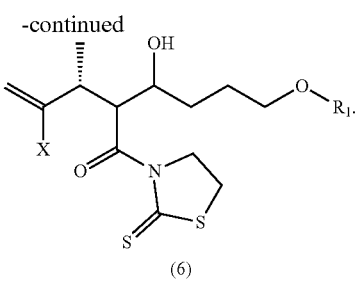

(6)

According to the invention, the reaction is performed in the presence of titanium tetrachloride (TiCl$_4$) and triethylamine (TEA), in an inert atmosphere, and at a relatively low temperature of −10 to 10° C., preferably 0° C. The solvent used in the reaction can be dichloromethane (DCM), etc.

According to the invention, the method for preparing the above aldehyde includes the following steps:

(I) reacting butanediol and R$_n$SiX$_{4-n}$ in the presence of coupling agents to obtain a monohydroxy protected product;

wherein X is halogen selected from the group consisting of chlorine, bromine and iodine, R is selected from the group consisting of C$_{1-10}$ alkyl or fluorinated C$_{1-10}$ alkyl, and n is an integer of 1-3. Examples of the halogenated silane R$_n$SiX$_{4-n}$ is TMSCl, TMSI, TBDPSCl, or TBDPSI, etc.

The coupling agents can be an EDCI/DMAP, EDC/DMAP, EDC/NHS, or DCC/NHS system, and the reaction is performed at 15 to 40° C., preferably at room temperature (20 to 25° C.). The solvent used in the reaction can be dichloromethane (DCM), tetrahydrofuran (THF), dimethylformamide (DMF), etc.

(II) Oxidizing the product obtained in step (I).

The oxidation is any method for oxidizing alcohols to aldehydes or ketones as described below.

According to the method for preparing the compound of Formula (8) of the invention, it further includes the following step: preparing the compound of Formula (7) from the compound of Formula (6):

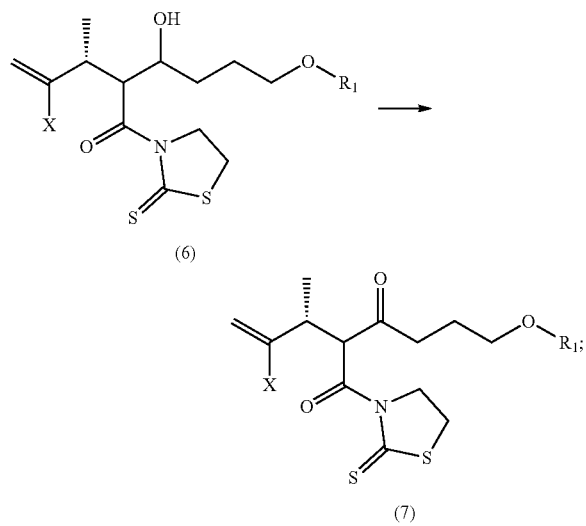

According to the invention, the oxidation of alcohols to aldehydes or ketones can be realized by any method known to those skilled in the art, such as Swern oxidation, Pfitzner-Moffatt oxidation, and Albright-Goldman oxidation. As an embodiment of the invention, the Parikh-Doering oxidation method is employed: dimethyl sulfoxide (DMSO) and sulfur trioxide-pyridine complex (SO$_3$·py) reacting with an alcohol at −15-25° C. and under basic conditions. The base can be triethylamine or N, N-diisopropyl ethylamine (DIPEA); the reaction temperature is preferably 0° C. to room temperature (room temperature is 20-25° C.); the solvent added in the reaction is optional depending on the added amount of DMSO, that is, a relatively large amount of solvent is required for a small amount of DMSO, while a small amount of solvent or no solvent is required for a large amount of DMSO. The solvent, for example, is dichloromethane, tetrahydrofuran, chloroform, etc.

According to the method for preparing the compound of Formula (8) of the invention, it further includes the following step: hydrolyzing the above compound of Formula (7) to obtain the compound of Formula (8) in which a carbonyl group is formed by R$_2$ and R$_3$ together with the carbon atom to which they are bonded.

According to the invention, the hydrolysis reaction is carried out at 15-40° C., under basic conditions and in a solvent medium. The reaction temperature can be room temperature (20-25° C.), and the base can be selected from organic bases, inorganic bases or mixtures thereof, such as one or more of potassium carbonate, sodium carbonate, potassium bicarbonate, sodium bicarbonate, cesium carbonate, lithium hydroxide, lithium hydroxide hydrate, sodium hydroxide, potassium hydroxide, calcium hydroxide, ammonia, sodium acetate, triethylamine, pyridine or piperidine. The solvent is a mixture of water and one or more of alcohols, ethers such as THF or dioxane, and acetone. The ratio (volume ratio) of water to organic solvents in the mixture can be about 1:1-1:6, preferably about 1:4. As an embodiment of the invention, the hydrolysis reaction is carried out at room temperature, in a mixed solvent of tetrahydrofuran and water, and in the presence of lithium hydroxide monohydrate.

According to the method for preparing the compound of Formula (8) of the invention, optionally, it includes the reaction step from the compound of Formula (6) further to form the compound of Formula (8) in which R$_2$ and R$_3$ are the same or different, and independently selected from H and OR$_a$, and R$_a$ is independently selected from H, C$_{1-10}$ alkyl, R$_b$SO$_2$, wherein R$_b$ is C$_{1-10}$ alkyl. The reaction is a hydroxylalkylation or sulfonation reaction known in the art.

According to the method for preparing the compound of Formula (8) of the invention, optionally, it includes the reaction step from the compound of Formula (8), in which a carbonyl group is formed by R$_2$ and R$_3$ together with the carbon atom to which they are bonded, further to form the compound of Formula (8) in which R$_2$ and R$_3$ are both OR$_a$, and two R$_a$ are bonded together to form C$_{1-6}$ alkylene. The reaction known in the art is used in a synthesis of ketals. For example, a ketone and the corresponding diol, such as glycol, propylene glycol, etc., react to obtain the ketal in the presence of p-toluenesulfonic acid as catalyst, and by using benzene or toluene as a water-carrying agent.

According to the invention, the compound of Formula (8) is for the synthesis of halichondrins, and particularly is the intermediate used for the synthesis of the C20-C26 fragment of eribulin or a pharmaceutically acceptable salt thereof.

The second aspect of the invention is to provide the compound of Formula (2) which is defined as follows and a method thereof:

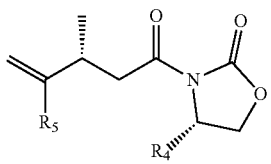

wherein $R_4$ and $R_5$ are defined as described above.

The method for preparing the compound of Formula (2) includes the above step of preparing the compound of Formula (2) from the compound of Formula (1).

According to the invention, the method for preparing the compound of Formula (2) further includes the above-mentioned step of recrystallizing once, twice or more times.

According to the invention, the method for preparing the compound of Formula (2) further includes the step of preparing the compound of Formula (1) from an oxazolidinone chiral auxiliary and the corresponding acyl compound.

The third aspect of the invention is to provide the compound of Formula (3) which is defined as follows and a method thereof:

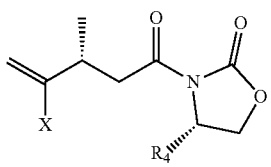

wherein $R_4$ and X are defined as described above.

The method for preparing the compound of Formula (3) includes the above step of preparing the compound of Formula (3) from the compound of Formula (2).

According to the invention, the method for the preparation further includes the method for preparing the above compound of Formula (2). Preferably, it further includes the step of recrystallizing the above compound of Formula (2) once, twice or more times.

Preferably, it further includes the step of preparing the compound of Formula (1) from an oxazolidinone chiral auxiliary and the corresponding acyl compound.

The fourth aspect of the invention is to provide the compound of Formula (7) which is defined as follows and a method thereof:

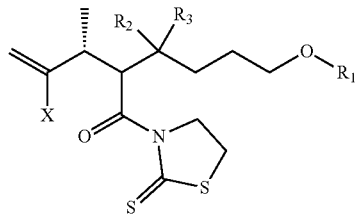

wherein, $R_1$ is selected from hydroxyl protecting groups; $R_2$ and $R_3$ are the same or different, and independently selected from H and $OR_a$, and $R_a$ is independently selected from the group consisting of H, $C_{1-10}$ alkyl, $R_bSO_2$, wherein $R_b$ is $C_{1-10}$ alkyl; or $R_2$ and $R_3$ are both $OR_a$, and two $R_a$ are bonded together to form $C_{1-6}$ alkylene; or $R_2$ and $R_3$ together with the carbon atom to which they are bonded form a carbonyl group;

X is selected from the group consisting of halogen, sulfonyloxy groups.

Preferably, $R_1$ is selected from the silyl hydroxyl protecting groups, such as TMS, TES, TBDMS, TBDPS, DIPS, DPS, TIPDS, etc.

One of $R_2$ and $R_3$ is selected from H, the other is selected from $OR_a$, and $R_a$ is H or i-$PrSO_2$; or $R_2$ and $R_3$ are both $OR_a$, and two $R_a$ are bonded together to form n-propylidene; or $R_2$ and $R_3$ together with the carbon atom to which they are bonded form a carbonyl group;

X is selected from the group consisting of chlorine, bromine, iodine, etc.

The method for preparing the compound of Formula (7) includes the following step:

Method 1: the compound of Formula (7) in which $R_2$ and $R_3$ together with the carbon atom to which they are bonded to form a carbonyl group is obtained by the oxidation of the compound of Formula (7) with $R_2$ and $R_3$ as H and OH respectively:

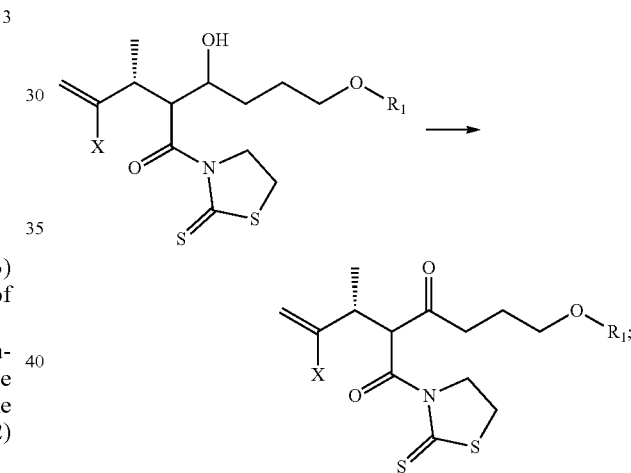

According to the invention, the oxidation of alcohols to aldehydes or ketones can be realized by any method known to those skilled in the art, such as Swern oxidation, Pfitzner-Moffatt oxidation, and Albright-Goldman oxidation. As an embodiment of the invention, the Parikh-Doering oxidation method is employed: dimethyl sulfoxide (DMSO) and sulfur trioxide-pyridine complex ($SO_3 \cdot py$) reacting with an alcohol at $-15\text{-}25°$ C. and under basic conditions. The base can be triethylamine or N, N-diisopropyl ethylamine (DIPEA); the reaction temperature is preferably $0°$ C. to room temperature (room temperature is $20\text{-}25°$ C.); the solvent added in the reaction is optional depending on the added amount of DMSO, that is, a relatively large amount of solvent is required for a small amount of DMSO, while a small amount of solvent or no solvent is required for a large amount of DMSO. The solvent, for example, is dichloromethane, tetrahydrofuran, chloroform, etc.

Method 2: the compound of Formula (7) with $R_2$ and $R_3$ as H and OH respectively is prepared from the following compound of Formula (5):

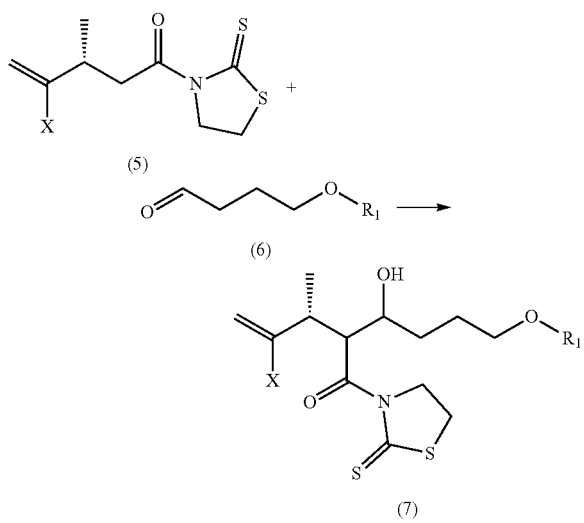

According to the invention, the reaction is performed in the presence of titanium tetrachloride (TiCl₄) and triethylamine (TEA), in an inert atmosphere, and at a lower temperature of −10 to 10° C., preferably 0° C. The solvent used in the reaction is selected from dichloromethane (DCM), etc.

The compounds of Formula (7) with other defined R$_2$ and R$_3$ can be prepared by common methods known in the art, such as substitution, condensation, etc., and obtained from the compound of Formula (7) in which R$_2$ and R$_3$ together with the carbon atom to which they are bonded to form a carbonyl group, or from the compound of Formula (7) with R$_2$ and R$_3$ as H and OH respectively.

The fifth aspect of the invention is also to provide the use of the compounds of Formula (2), Formula (3), and Formula (7), which are used for the preparation of halichondrins, particularly eribulin, pharmaceutically acceptable salts and analogs thereof. Specifically, the compounds of Formula (2), Formula (3) and Formula (7) are used for preparing the compound of Formula (8) which is used for the synthesis of halichondrins, and particularly is the intermediate for the C20-C26 fragment of eribulin.

The sixth aspect of the invention is to provide a method for preparing the compound of Formula (8), the method including the following step:

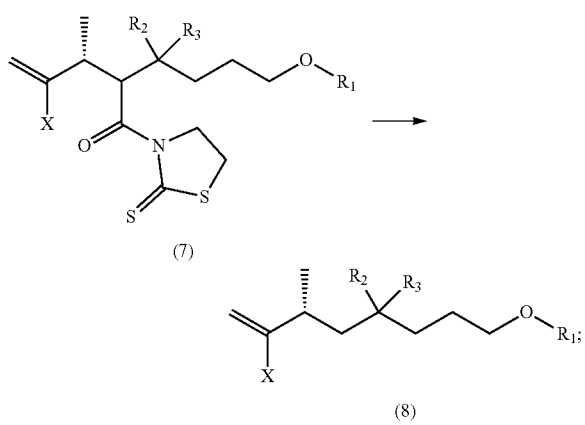

According to the method for preparing the compound of Formula (8) of the invention, preferably, it also includes the step of the oxidation of the compound of Formula (7) with R$_2$ and R$_3$ as H and OH respectively to form the compound of Formula (7) in which R$_2$ and R$_3$ together with the carbon atom to which they are bonded to form a carbonyl group:

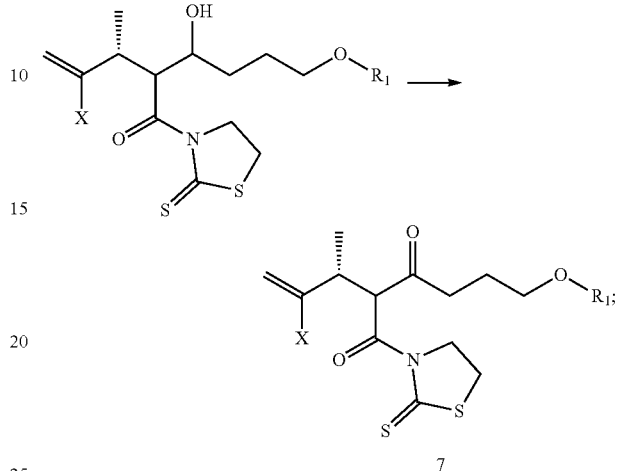

preferably, it also includes the step of the preparation of the compound of Formula (7) with R$_2$ and R$_3$ as H and OH respectively from the compound of Formula (5) and the compound of Formula (6):

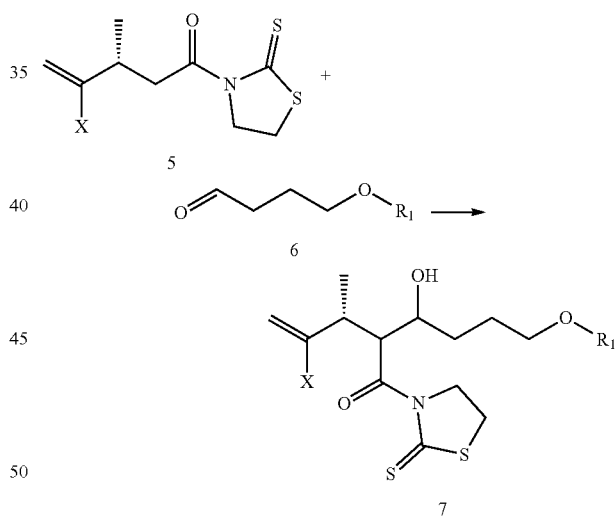

preferably, it also includes the above step of preparing the compound of Formula (5) from the compound of Formula (4);

preferably, it also includes the above step of preparing the compound of Formula (4) from the compound of Formula (3);

preferably, it also includes the above step of preparing the compound of Formula (3) from the compound of Formula (2);

preferably, it also includes the above step of preparing the compound of Formula (2) from the compound of Formula (1);

preferably, it also includes the step of recrystallizing the compound of Formula (2) once, twice or more times;

preferably, it further includes the above step of preparing the compound of Formula (1) from the oxazolidinone chiral auxiliary.

The seventh aspect of the invention is to provide the method for preparing halichondrins, eribulin, analogs or pharmaceutically acceptable salts thereof, or the C20-C26 fragment, including using the above oxazolidinone chiral auxiliary, any compound of Formula (1) to Formula (7), and/or one or more reaction steps in the above methods for preparing the compound of Formula (1) to the compound of Formula (8).

The invention also provides the use of the above oxazolidinone chiral auxiliary and any compound of Formula (1) to Formula (7) in preparing halichondrins, eribulin, analogs, or the C20-C26 fragment.

The symbols of the compounds, the definitions of the groups and the reaction conditions, as described in above, unless specified otherwise, have the same definitions or meanings as the above.

Definition and Description of Terms:

Unless defined otherwise, all technical and scientific terms used herein have the same meaning as commonly understood by one of ordinary skill in the art to which the subject matter of the claims belongs. Unless stated otherwise, all patents, patent applications, and the entire contents of published materials cited herein are incorporated herein as a whole by reference.

When the numerical ranges described in the specification and claims of the patent application are understood as "integers", it should be understood that two endpoints of the ranges and each integer within the ranges are disclosed. For example, "integers from 0 to 10" should be understood that each of the integers 0, 1, 2, 3, 4, 5, 6, 7, 8, 9, and 10 is disclosed. When the numerical ranges are understood as "numbers", it should be understood that two endpoints of the ranges, each integer within the ranges and each decimal within the ranges are disclosed. For example, "numbers from 1 to 10" should be understood that not only each of the integers 1, 2, 3, 4, 5, 6, 7, 8, 9 and 10, but also at least the sum of each integer and 0.1, 0.2, 0.3, 0.4, 0.5, 0.6, 0.7, 0.8, 0.9, respectively is disclosed.

The term "halichondrin, halichondrin analog" should be understood as a substance having a polyether macrolide structure, the structure containing the C20-C26 fragment of eribulin. For example, eribulin, norhalichondrin A-C, halichondrin B-C, homohalichondrin A-C, or its pharmaceutically acceptable salts, for instance, the salts formed with pharmaceutically acceptable acids, such as methanesulfonate, e.g., eribulin methanesulfonate.

The term "$C_{1-10}$ alkyl" should be understood to refer preferably to a straight or branched-chain saturated monovalent hydrocarbon group having 1, 2, 3, 4, 5, 6, 7, 8, 9, or 10 carbon atoms. The alkyl group is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl or their isomers. In particular, the group has 1, 2, 3, 4, 5, 6 carbon atoms ("$C_{1-6}$ alkyl"), such as methyl, ethyl, propyl, butyl, isopropyl, isobutyl, sec-butyl, tert-butyl, and more particularly, the group has 1, 2 or 3 carbon atoms ("$C_{1-3}$ alkyl"), such as methyl, ethyl, n-propyl or isopropyl.

The term "$C_{1-6}$ alkylene" should be understood to refer preferably to a straight or branched-chain saturated divalent hydrocarbon group having 1, 2, 3, 4, 5 or 6 carbon atoms, such as methylene, ethylene, n-propylidene, isopropylidene, etc.

The term "hydroxyl protecting group" means any group capable of protecting the oxygen atom to which it is attached from reacting or bonding. Hydroxyl protecting groups are known in the art. Exemplary hydroxyl protecting groups include, but are not limited to, acyl, ester, carbonate, urethane, sulfonate, and ether groups.

As defined herein, exemplary ether hydroxyl protecting groups include $C_{1-12}$ alkyl groups (e.g., $C_{1-8}$, $C_{1-6}$, $C_{1-4}$, $C_{2-7}$, $C_{3-12}$ and $C_{3-6}$ alkyl), and silyl groups (e.g., tris($C_{1-6}$ alkyl)silyl, tris($C_{6-10}$ aryl or $C_{1-6}$ heteroaryl)silyl, bis($C_{6-10}$ aryl or $C_{1-6}$ heteroaryl)($C_{1-6}$ alkyl) silyl, and ($C_{6-10}$ aryl or $C_{1-6}$ heteroaryl)bis($C_{1-6}$ alkyl) silyl). Specific examples of alkyl include methyl and tert-butyl, and specific examples of silyl include trimethylsilyl (TMS), triethylsilyl (TES), tert-butyldimethylsilyl (TBS), tert-butyldiphenylsilyl (TBDPS), triisopropylsilyl (TIPS) and triphenylsilyl (TPS) ether groups, TBDMS, DIPS, DPS, TIPDS, etc.

The hydroxyl protecting groups, as defined above, can be deprotected with deprotecting reagents. The deprotecting reagents used for removing the hydroxyl protecting groups are those reagents that can react with compounds with hydroxyl protecting groups to provide compounds with deprotected hydroxyl groups. The deprotecting reagents used for removing the hydroxyl protecting groups and the deprotection reaction conditions can be known in the art. In one non-limiting embodiment, protected hydroxyl groups as silyl ethers may be deprotected by reacting with fluoride compounds (e.g., a fluoride salt, such as KF or TBAF). Alternatively, the protected hydroxyl groups as TMS or TES ethers may be deprotected by reacting with Bronsted acids (e.g., carboxylic acid). In another non-limiting embodiment, the protected hydroxyl groups as esters can be deprotected by reacting with $C_{1-6}$ alkoxides (e.g., alkali metal $C_{1-6}$ alkoxides or alkaline earth metal $C_{1-6}$ alkoxides). In another non-limiting embodiment, the protected hydroxyl groups as arylalkyl ethers (e.g., 1-arylalk-1-yl ether) may be deprotected by using a reduction reaction (e.g., with Pd/C and $H_2$, or with Na/$NH_3$). Alternatively, the protected hydroxyl groups as alkoxy-arylalkyl ethers (e.g., MPM ethers) can be deprotected by reacting with 2,3-dichloro-5,6-dicyano-1,4-benzoquinone (DDQ). In another non-limiting embodiment, the protected hydroxyl groups as alkoxyalkyl ethers (e.g., 1-alkoxyalk-1-yl) or THP ethers can be deprotected by reacting with Bronsted acids. The protected cyclic diols (such as acetals or ketals (e.g., 2-alkyl-1,3-dioxolanes, 2,2-dialkyl-1,3-dioxolanes, 2-alkyl-1,3-dioxanes or 2,2-dialkyl-1,3-dioxanes) can be deprotected by reacting with Bronsted acids (e.g., carboxylic acid).

The sulfonyloxy groups of the invention can be alkylsulfonyloxy groups (e.g., $C_{1-10}$ alkyl), alkenylsulfonyloxy groups (e.g. $C_{2-10}$ alkenyl), arylsulfonyloxy groups. The embodiments include, but are not limited to: methanesulfonyloxy, toluenesulfonyloxy (e.g., p-toluenesulfonyloxy), trifluoromethanesulfonyloxy, nitrobenzenesulfonyloxy (o, p-nitrobenzenesulfonyloxy), bromobenzenesulfonyloxy(o, p-bromobenzenesulfonyloxy).

The methylsilyl group of the invention can be tri($C_{1-6}$ alkyl)silyl, tri($C_{6-10}$ aryl or $C_{6-10}$ heteroaryl)silyl, di($C_{6-10}$ aryl or $C_{6-10}$ heteroaryl) ($C_{1-6}$ alkyl)silyl and ($C_{6-10}$ aryl or $C_{6-10}$ heteroaryl)di($C_{1-6}$ alkyl)silyl. Specific examples of silyl include, but are not limited to, trimethylsilyl (TMS), triethylsilyl (TES), t-butyldimethylsilyl (TBS), t-butyldiphenylsilyl (TBDPS), triisopropylsilyl (TIPS) and triphenylsilyl (TPS), TBDMS, DIPS, DPS, TIPDS, etc.

The suitable substituents on phenyl or benzyl groups of the invention include, but are not limited to, halogen (fluoro, chloro, bromo, iodo), $C_{1-10}$ alkyl, $C_{1-10}$ alkoxy, hydroxy, nitro, amino, amino substituted by one or two $C_{1-10}$ alkyl groups, $SO_3H$, $SO_3C_{1-10}$ alkyl groups.

The bases of the invention can be organic bases, inorganic bases or mixtures thereof, for example, selected from alkali metal or alkaline earth metal carbonates or bicarbonates, such as lithium carbonate, sodium carbonate, potassium carbonate, calcium carbonate, cesium carbonate, sodium bicarbonate, potassium bicarbonate, calcium bicarbonate; alkali metal alkoxides, such as sodium t-butanoxide or potassium t-butanoxide; organic lithium, such as butyl lithium or phenyl lithium; alkali metal hydrides, such as sodium hydride or potassium hydride; amines, such as lithium bis(trimethylsilyl)amide, potassium bis(trimethylsilyl) amide or lithium diisopropylamide (LDA); organic amines, such as triethylamine, N-methylmorpholine, piperidine, N-methylpiperidine, N,N-diisopropylethylamine, 1,5-diazabicyclo[4.3.0]non-5-ene (DBN), 1,8-diazabicyclo[5.4.0]undec-7-ene (DBU), pyridine or 4-dimethylaminopyridine (DMAP).

The acids of the invention can be organic acids, inorganic acids or mixtures thereof, for example, selected from one or more of the following acids: hydrochloric acid, sulfuric acid, phosphoric acid, nitric acid; carboxylic acid, such as acetic acid or trifluoroacetic acid; sulfonic acid, such as methanesulfonic acid, trifluoromethylsulfonic acid or p-toluenesulfonic acid; phosphonic acid; hydrochloric acid, sulfuric acid, phosphoric acid. The acids also include Lewis acid. The Lewis acids can be one or more selected from $BF_3 OEt_2$, $MgCl_2$, $MgBr_2$, $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2$, $SnCl_4$, $TiCl_4$, $TiCl_3$, $MnCl_2$, $ScCl_3$, $AlCl_3$, $(i-C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$ or trimethylsilyl trifluoromethanesulfonate. The specific examples can be one or more selected from $BF_3·OEt_2$, $MgCl_2$, $ZnCl_2$, $MgBr_2$, $ZnBr_2$, $AlCl_3$, $SnCl_4$, $TiCl_4$ or trimethylsilyl trifluoromethanesulfonate.

The solvents of the invention can be selected from, for example, one or a mixture of two or more of the following: water; ketone solvents, such as acetone and methyl ethyl ketone; ether solvents, including acyclic ethers and cyclic ethers, such as diethyl ether, tetrahydrofuran, dioxane; ester solvents, such as ethyl acetate or butyl acetate; alkane solvents, such as n-hexane or n-heptane; halogenated alkane solvents, such as monochloromethane, dichloromethane, chloroform, carbon tetrachloride, 1,2-dichloroethane; cycloalkane solvents, such as cyclohexane or cycloheptane; substituted or unsubstituted aromatic solvents, such as benzene, toluene, xylene, chlorobenzene; alcohol solvents, such as methanol, ethanol, n-propanol, isopropanol, n-butanol or t-butanol; or other solvents, such as N, N-dimethylformamide (DMF), dimethyl sulfoxide (DMSO), N-methylpyrrolidone (NMP), acetonitrile or pyridine. Preferably, the solvents are selected from inert solvents which have no reaction activity to the reaction substrates and catalysts. As an example, the inert solvents can be one or more selected from, for example, alcohol solvents (e.g., methanol, ethanol), ether solvents (e.g., diethyl ether, tetrahydrofuran, dioxane), halogenated alkane solvents (e.g., dichloromethane, trichloromethane, carbon tetrachloride, 1,2-dichloroethane), substituted or unsubstituted aromatic hydrocarbons (e.g., benzene, toluene, chlorobenzene).

Unless specified otherwise, the solvents of the invention are anhydrous solvents.

Beneficial Effects

The invention provides intermediates for preparing halichondrins, eribulin, or their analogs, and particularly the intermediates with the C20-C26 fragment, the methods and use thereof. The raw materials used in the synthetic routes of the invention are cheap and easily obtained. The compounds of Formula (2) and Formula (3) are both crystals, and the purity of which can be improved by recrystallization which is a simple method of purification. In particular, after the compound of Formula (2) is recrystallized twice, the optical purity can be achieved to be greater than 99.9%. The configuration of the chiral carbon atom, attached to the methyl group at the β position of the compound, does not change in the subsequent steps, ensures optical purities of the C20-C26 fragment of halichondrins, eribulin or their analogs. Therefore, the method for constructing the chiral center of the C20-26 fragment of the invention has advantages of high diastereoselectivity and high yield, and by-products can only be removed by simple methods such as recrystallization. All the steps of the methods are carried out at relatively low temperature and under mild reaction conditions. Particularly in the step of preparing the compound of Formula (8) from the compound of Formula (7) the loss of the product is avoided due to the thermal decomposition at a high temperature. The products obtained by the entire preparation methods, especially in the front-end steps, are all crystalline solids to be easily purified and refined. Based on the above advantages, i.e., low cost, high yield and high product purity, simple processes of refining and purification, the methods of the invention are more suitable for large-scale industrialized production.

BRIEF DESCRIPTION OF THE DRAWING

FIG. 1: Schematic illustration of synthetic routes in Example 1 of the invention.

EXAMPLES

The above and other features and advantages of the invention are explained and illustrated in more detail in the following by describing the examples of the invention. It should be understood that the following examples are intended to give an exemplary description of the technical solutions of the invention, rather than any limitation on the scope of protection of the invention as defined by the claims and their equivalents.

Unless otherwise specified, the materials and reagents herein are commercially available products or can be prepared by those skilled in the art according to the prior art.

It should be understood by those skilled in the art that the raw materials, reagents, intermediates, target compounds or reactions in the following examples are all exemplary technical solutions of the above-mentioned compounds of general formula or their reactions, one or more of the specific compounds or reactions can be combined with the above general technical solutions of the invention, and the combined technical solutions should be understood as the technical solutions described in the specification.

Unless otherwise specified, the yields in the following examples are acceptable as the purities of products are more than 99.5%.

Example 1: Method 1 for Preparing Compound 8
(See FIG. 1)

1.1 Preparation of Compound 1
Method 1

(S)-4-phenyl-2-oxazolidinone (15.6 g) was added into a 500 mL three-necked flask, and dissolved by adding dry THF (200 mL). The solution was purged with argon for protection, then cooled to −78° C., and added with a solution of n-BuLi in THF (2.5 M, 38 mL) dropwise (The internal temperature was maintained not more than −60° C.). The reaction was kept at −78° C. for 15 mins after the dropwise addition. The mixture was added with crotonoyl chloride (10 g), and the reaction was kept at −78° C. for 30 mins after the dropwise addition. Then the temperature was increased to 0° C. and the reaction was kept for 1.5 hours. After completion of the reaction detected by TLC, the solution was quenched by slowly adding a saturated solution of ammonium chloride. The mixture was stirred well until the solid was completely dissolved and clearly layered. The layers were separated. The aqueous phase was extracted twice with ethyl acetate. The organic phases were combined. The combined organic phase was washed once with a saturated sodium chloride solution, dried by adding anhydrous sodium sulfate, and filtered. The filtrate was concentrated. The obtained concentrate was added with ethyl acetate (100 mL), and dissolved by heating under reflux. Crystals were precipitated when the solution was added with n-hexane (500 mL), cooled down, and stirred. After filtration, 17.7 g of a white solid product with a yield of 80% was obtained.

Method 2:

(S)-4-phenyl-2-oxazolidinone (60 g) was added into a 2000 mL three-necked flask, and dissolved by adding with non-anhydrous THF (1200 mL). LiCl (26.4 g) and TEA (91.2 mL) was added into the solution at room temperature, and then crotonic anhydride (82.2 mL) was added dropwise. The internal temperature was maintained not more than 25° C. After the dropwise addition, the reaction was kept at room temperature for 3 hours. Until the spots of the starting material of (S)-4-phenyl-2-oxazolidinone disappeared that was monitored by TLC, water (800 mL) was added to dissolve the solid in the reaction solution. The solution was layered, and separated. The aqueous phase was extracted twice with ethyl acetate. The organic phases were combined. The combined organic phase was washed once with a saturated sodium chloride solution, dried by adding anhydrous sodium sulfate, and filtered. The filtrate was concentrated. The obtained concentrate was added with ethyl acetate (400 mL), and dissolved by heating under reflux. Crystals were precipitated when the solution was added with n-hexane (2000 mL), cooled down, and stirred. After filtration, 72 g of a white solid product with a yield of 85% was obtained.

$^1$H NMR (400 MHz,) δ 7.44-7.23 (m, 6H), 7.21-6.96 (m, 1H), 5.47 (dd, J=8.7, 3.9 Hz, 1H), 4.68 (t, J=8.8 Hz, 1H), 4.26 (dd, J=8.9, 3.9 Hz, 1H), 1.92 (dd, J=6.9, 1.6 Hz, 3H).

1.2 Preparation of Compound 2

1) Preparation of (1-Bromovinyl)Trimethylsilane

Vinyltrimethylsilane (100 g) was added into a 2000 mL three-necked flask, and then cooled between −35° C. and −30° C. Bromine water was slowly added dropwise, while heat was violently released. The internal temperature was maintained between −30° C. and −10° C. during the dropwise addition (when the internal temperature was lower than −30° C., the reaction system became solid). After the dropwise addition, the temperature rose naturally to room temperature. Diethylamine (676 mL) was slowly added. At the beginning of the addition, heat was released. After the dropwise addition, the reaction solution was heated under reflux for 1.2 hours. After the completion of reaction, the reaction solution was cooled to room temperature, and diluted by adding with diethyl ether (1000 mL), washed 2-3 times with water and then with 2N hydrochloric acid until the pH value of the aqueous layer to 1. The organic phase was successively washed once with saturated sodium bicarbonate and once with saturated sodium chloride, dried with anhydrous sodium sulfate, and filtered. The filtrate was concentrated. The concentrate was distilled under reduced pressure. 80 g of the fraction (between 38° C. to 42° C.) was collected. The yield was 45%.

$^1$H NMR (400 MHz, Chloroform-d) δ 6.27 (s, 1H), 6.19 (s, 3H), 0.20 (s, 9H).

2) Preparation of Compound 2

Mg particles (8.4 g) and iodine particles (1-2 particles) were added into a three-necked flask, and the flask was purged with argon for protection. (1-bromovinyl)trimethylsilane (62.7 g) was dissolved in dry THF (159 mL), and part of the solution (20 mL) was added into the above three-necked flask at room temperature. The three-necked flask was heated. When the reaction was initiated in the flask, and the reaction mixture was refluxed, the THF solution was continuously added dropwise. The reaction solution was kept under refluxing. After the dropwise addition, the reaction flask was placed in an oil bath and the reaction solution was heated under refluxing for 1 h. A Grignard reagent was prepared.

CuI (6.69 g) was added into a 1000 mL three-necked flask, and THF was added. The flask was purged with argon for protection. The solution was cooled to −40° C., and the above Grignard reagent was added dropwise. The internal temperature was maintained not more than −30° C. After the dropwise addition, the reaction was kept at −40° C. for 0.5 h. A solution of compound 1 in THF (40.45 g/40 mL THF) was then added dropwise. After the addition, the temperature was increased to 0° C. and the reaction mixture was reacted for 2 hours. Until the spots of compound 1 disappeared that was monitored by TLC, the reaction solution was quenched by slowly adding a saturated solution of ammonium chloride, stirred vigorously for 4-6 hours to give two clear phases. The layers were separated. The aqueous phase was extracted twice with ethyl acetate. The organic phases were combined. The combined organic phase was washed twice with a saturated sodium chloride solution, dried by adding anhydrous sodium sulfate, and filtered. The filtrate was concentrated to obtain 57 g of a crude product. The crude product was dissolved in 570 mL n-hexane at room temperature. The solution was placed in a refrigerator at −20° C., and let stand while crystals were precipitated. The next day, the solution was filtered when cold. The filtrate was washed with cold n-hexane to give 42 g of a white solid. After secondary recrystallization, a product with a purity of 99.94% was obtained.

$^1$H NMR (500 MHz, Chloroform-d) δ 7.63-7.26 (m, 5H), 5.74 (d, J=1.9 Hz, 1H), 5.51 (dd, J=8.7, 3.8 Hz, 1H), 5.42 (d, J=2.2 Hz, 1H), 4.76 (t, J=8.8 Hz, 1H), 4.35 (dd, J=9.0, 3.8 Hz, 1H), 3.30 (q, J=9.4 Hz, 1H), 3.08-2.84 (m, 2H), 1.09 (d, J=6.2 Hz, 3H), 0.12 (s, 9H).

1.3 Preparation of Compound 3

Iodine (43.2 g) was dissolve in DCM (752 mL), and the raw material 2 (18.8 g) was added in batches at 0° C. After the addition, the temperature was increased to room temperature and the mixture was reacted for about 12-20 hours. When the spots of the raw material disappeared that was monitored by TLC, the reaction mixture was quenched by adding a saturated sodium sulfite solution, stirred vigorously until the purple color of the solution faded and became colorless. The solution layers were separated. The aqueous layer was extracted once with DCM. The organic phases were combined and dried by adding anhydrous sodium sulfate. The combined organic phase was filtered. The filtrate was concentrated to give 20 g of a crude product. The crude product was purified by column chromatography to obtain 15 g of a product. The product was heated and dissolved in a mixed solvent of n-hexane and ethyl acetate (70 mL). Crystals were precipitated when the solution was cooled down and stirred. 9.4 g of a white solid with a yield of 43% was obtained.

$^1$H NMR (500 MHz, Chloroform-d) δ 7.41-7.27 (m, 5H), 6.09 (d, J=1.6 Hz, 1H), 5.62 (d, J=1.6 Hz, 1H), 5.43 (dd, J=8.8, 4.0 Hz, 1H), 4.70 (t, J=8.8 Hz, 1H), 4.27 (dd, J=9.0, 4.0 Hz, 1H), 3.23 (dd, J=16.9, 6.6 Hz, 1H), 2.85 (dd, J=16.9, 7.0 Hz, 1H), 2.56 (q, J=6.8 Hz, 1H), 1.04 (d, J=6.7 Hz, 3H).

1.4 Preparation of Compound 4

The raw material 3 (14.27 g) was dissolved in a mixed solution of THF-H$_2$O (148 mL-37 mL). The mixture was then cooled to about −5° C., successively added with hydrogen peroxide (35%, 15.8 mL) and an aqueous solution of lithium hydroxide monohydrate (3.1 g/30 mL H$_2$O) dropwise. After the dropwise addition, the reaction was kept at 0° C. for 2 hours. When the spots of the raw material disappeared that was monitored by TLC, the temperature of the reaction solution was increased to room temperature. A saturated solution of sodium sulfite was slowly added, until the potassium iodide starch test papers did not change color. THF was removed by distillation under reduced pressure. The aqueous phase was washed 2-3 times with DCM, until no more (S)-4-phenyl-2-oxazolidinone. The aqueous phase was added into a round-bottom flask, cooled to 0° C., and the pH of the aqueous phase was adjusted to 1 with a 10% diluted solution of hydrochloric acid. Then the solution was extracted 2-3 times with DCM, dried, and filtered. The filtrate was concentrated to obtain compound 4.

$^1$H NMR (400 MHz, Chloroform-d) δ 6.21 (s, 1H), 5.90-5.59 (m, 1H), 2.62-2.54 (m, 1H), 2.54-2.46 (m, 1H), 2.31 (dd, J=15.0, 6.4 Hz, 1H), 1.11 (d, J=6.5 Hz, 3H).

1.5 Preparation of Compound 5

The above obtained compound 4 was dissolved in DCM (185 mL), to which thiazoline-2-thione (4.84 g), EDCI (8.86 g) and DMAP (0.7 g) were added at room temperature. The reaction was kept at room temperature for 4-6 hours. When the spots of the raw material disappeared that was monitored by TLC, the reaction mixture was quenched by adding a saturated sodium bisulfate solution, and stirred. The solution layers were separated. The aqueous phase was extracted twice with DCM, and the organic phases were combined. The combined organic phase was successively washed with a saturated sodium bicarbonate solution and with a saturated sodium chloride solution, then dried by adding anhydrous sodium sulfate, and filtered. The filtrate was concentrated. The concentrate was purified by column chromatography to obtain 10.06 g of a yellow syrup-like product (solidified during standing or freezing) with a yield of 80%.

$^1$H NMR (400 MHz, Chloroform-d) δ 6.22 (dd, J=1.6, 0.9 Hz, 1H), 5.76 (d, J=1.7 Hz, 1H), 4.65-4.45 (m, 2H), 3.47 (dd, J=17.1, 7.3 Hz, 1H), 3.35-3.22 (m, 2H), 1.10 (d, J=6.7 Hz, 3H).

1.6 Preparation of Compound 6

1) Preparation of 4-((t-butyldiphenylsilyl)oxy)butanal

Step 1: 1,4-butanediol (100 mL) was added into a 2000 mL three-necked flask at room temperature, to which DCM (1300 mL), triethylamine (59 mL) and DMAP (4.7 g) were added, and then TBSCl was slowly added dropwise. After the dropwise addition, the reaction was kept at room temperature overnight (about 17 hours). When the spots of the raw material TBSCI disappeared that was monitored by TLC, the reaction mixture was quenched by adding a saturated solution of ammonium chloride. The solution layers were separated. The aqueous layer was extracted twice with DCM, and the organic phases were combined. The combined organic phase was washed once with a saturated sodium chloride solution, dried by adding anhydrous sodium sulfate, and filtered. The filtrate was concentrated. The concentrate was purified by column chromatography to obtain 108 g of a syrup-like product with a yield of 80%.

$^1$H NMR (400 MHz, Chloroform-d) δ 7.89-7.56 (m, 4H), 7.53-7.35 (m, 6H), 3.68 (dt, J=15.2, 5.9 Hz, 4H), 1.74-1.59 (m, 4H), 1.05 (s, 9H).

Step 2: 4-((tert-butyldiphenylsilyl)oxy)butanol (11.6 g) was dissolved in dry DCM (71 mL), and then cooled to 0° C. The solution was successively added with dry DMSO (12.6 mL) and DIPEA (15.4 mL), and added with sulfur trioxide-pyridine (11.3 g) in batches. The internal temperature was maintained not more than 10° C. After the addition, the temperature was increased to room temperature and the mixture was reacted for 0.5-1 h. When the spots of the raw material disappeared that was monitored by TLC, the reaction mixture was quenched by adding water, washed once with 1N diluted hydrochloric acid. The aqueous layer was extracted once with DCM, and the organic phases were combined. The combined organic phase was successively washed once with a saturated sodium bicarbonate solution and with a saturated sodium chloride solution, dried with anhydrous sodium sulfate, and filtered. The filtrate was concentrated to obtain a syrup-like product, which was directly used in the next reaction, so it was freshly prepared just before use.

$^1$H NMR (400 MHz, Chloroform-d) δ 9.79 (s, 1H), 7.65 (t, J=7.6 Hz, 4H), 7.52-7.30 (m, 6H), 3.79-3.49 (m, 2H), 2.55 (d, J=6.7 Hz, 2H), 1.88 (t, J=8.3 Hz, 2H), 1.04 (s, 9H).

2) The raw material 5 (10.1 g) was added into a 1000 mL three-necked flask, dissolved by adding dry DCM. The flask was purged with argon for protection. The reaction solution was then cooled to 0° C., to which titanium tetrachloride (3.4 mL) was added dropwise, and triethylamine (3.58 mL) was rapidly added. The reaction was kept at 0° C. for 1 h. A DCM solution of 4-((t-butyldiphenylsilyl)oxy)butanal (11 g/20 mL) was added dropwise. After the dropwise addition, the reaction was kept at 0° C. for 4-6 hours. The reaction mixture was quenched by adding a saturated sodium chloride solution. The solution layers were separated. The aqueous layer was extracted twice with DCM, and the organic phases were combined. The combined organic phase was successively washed twice with a saturated sodium bicarbonate solution and once with a saturated sodium chloride solution, dried with anhydrous sodium sulfate, and filtered. The filtrate was concentrated. The concentrate was purified by column chromatography to obtain 13.1 g of a yellow syrup-like product with a yield of 84%.

Compound 6 Containing Four Diastereomers

Isomer A: $^1$H NMR (400 MHz, Chloroform-d) δ 7.65 (ddd, J=7.9, 4.3, 1.8 Hz, 4H), 7.44-7.35 (m, 6H), 6.37 (dd, J=1.3, 0.6 Hz, 1H), 5.84 (d, J=1.4 Hz, 1H), 5.26 (dd, J=10.0, 3.8 Hz, 1H), 4.56 (td, J=7.4, 5.8 Hz, 2H), 3.69 (t, J=6.1 Hz, 3H), 3.23-3.07 (m, 2H), 2.85 (d, J=10.1 Hz, 1H), 2.67 (dd, J=9.9, 6.6 Hz, 1H), 1.88-1.56 (m, 3H), 1.07 (d, J=6.7 Hz, 3H), 1.04 (s, 9H).

Isomer B: $^1$H NMR (400 MHz, Chloroform-d) δ 7.72-7.63 (m, 4H), 7.45-7.34 (m, 6H), 6.17 (s, 1H), 5.76-5.73 (m, 1H), 4.74 (dd, J=10.3, 3.4 Hz, 1H), 4.56 (ddd, J=11.9, 7.5, 2.1 Hz, 1H), 4.38-4.26 (m, 1H), 3.72-3.62 (m, 3H), 3.41 (ddd, J=12.3, 11.0, 7.5 Hz, 1H), 3.13 (ddd, J=10.9, 7.3, 2.1 Hz, 1H), 2.87 (d, J=10.9 Hz, 1H), 2.67 (dd, J=10.3, 6.4 Hz, 1H), 2.21-2.06 (m, 1H), 1.97-1.72 (m, 2H), 1.15 (d, J=5.7 Hz, 3H), 1.04 (s, 9H).

Characteristic peak of isomer C: $^1$H NMR (400 MHz, Chloroform-d) δ 6.22 (dt, J=1.8, 0.9 Hz, 1H), 5.72 (d, J=1.5 Hz, 1H), 5.38 (dd, J=9.7, 5.3 Hz, 1H).

Characteristic peak of isomer D: $^1$H NMR (400 MHz, Chloroform-d) δ 6.19-6.18 (m, 1H), 5.76-5.75 (m, 1H), 4.96 (dd, J=10.6, 5.2 Hz, 1H).

1.7 Preparation of Compound 7

The raw material 6 (13.07 g) was dissolved in dry DCM (40 mL), and then cooled to 0° C. The solution was successively added with dry DMSO (6.95 mL) and DIPEA (8.54 mL), and added with sulfur trioxide-pyridine (6.23 g) in batches. The internal temperature was maintained not more than 10° C. After the addition, the temperature was increased to room temperature and the mixture was reacted for 0.5-1 h. When the spots of the raw material disappeared that was monitored by TLC, the reaction mixture was quenched by adding water, and washed once with 1N diluted hydrochloric acid. The aqueous layer was extracted once with DCM, and the organic phases were combined. The combined organic phase was successively washed once with a saturated sodium bicarbonate solution and with a saturated sodium chloride solution, dried with anhydrous sodium sulfate, and filtered. The filtrate was concentrated to give a syrup-like product, which was purified by column chromatography to obtain 10.4 g of a product with a yield of 80%.

$^1$H NMR (400 MHz, Chloroform-d) δ 7.92-7.54 (m, 10H)(A/B), 7.39 (q, J=7.8, 7.1 Hz, 10H) (A/B), 6.25 (d, J=8.5 Hz, 1H) (A), 6.21 (s, 2H) (A/B), 5.77 (d, J=1.7 Hz, 1H) (A), 5.75 (d, J=1.7 Hz, 1H) (B), 5.07 (d, J=9.4 Hz, 1H)(A), 4.61-4.08 (m, 2H) (A/B), 4.26-4.05 (m, 2H) (A/B), 3.69-3.61 (m, 4H) (A/B), 3.33-3.13 (m, 4H) (A/B), 3.00-2.86 (m, 1H)(A), 2.79 (dt, J=15.2, 7.8 Hz, 5H) (A/B), 1.81 (q, J=6.9 Hz, 3H) (A), 1.12 (d, J=6.7 Hz, 3H) (A), 1.09 (d, J=6.5 Hz, 2H) (B), 1.05 (s, 18H) (A/B).

1.8 Preparation of Compound 8

The raw material 7 (10.4 g) was dissolved in a mixed solvent of THF and H$_2$O (120 mL/30 mL). The solution was added with lithium hydroxide monohydrate (6.54 g) at room temperature. The reaction mixture was kept at room temperature and stirred for 6-8 hours. After the completion of reaction, the reaction mixture was added with water. The solution layers were separated. The aqueous layer was extracted with n-hexane, and the THF layer was concentrated under reduced pressure. The concentrate was then dissolved by adding n-hexane. The organic phases were combined. The combined organic phase was washed with a saturated sodium dihydrogen phosphate, and with a saturated sodium chloride solution, dried with anhydrous sodium sulfate, and filtered. The filtrate was concentrated. The concentrate was purified by column chromatography to obtain 7.08 g of a product with a yield of 87%.

$^1$H NMR (400 MHz, Chloroform-d) δ 7.65 (dd, J=7.8, 1.5 Hz, 5H), 7.54-7.27 (m, 5H), 6.16 (dd, J=1.5, 0.8 Hz, 1H), 5.70 (d, J=1.7 Hz, 1H), 3.78-3.55 (m, 2H), 2.63 (dd, J=16.4, 6.5 Hz, 1H), 2.52 (td, J=7.1, 1.5 Hz, 3H), 2.29 (dd, J=16.3, 6.6 Hz, 1H), 1.88-1.75 (m, 2H), 1.05 (s, 9H), 1.02 (d, J=6.5 Hz, 3H).

The invention claimed is:

1. A method for preparing a compound of Formula (8), comprising:
hydrolyzing a compound of Formula (7) in a solvent to obtain the compound of Formula (8):

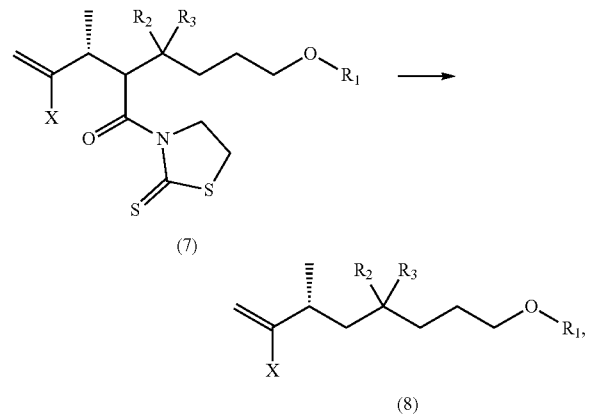

wherein, $R_1$ is a hydroxyl protecting group;
$R_2$ and $R_3$ are the same or different, and independently selected from H and $OR_a$, and $R_a$ is independently selected from the group consisting of H, $C_{1-10}$ alkyl, $R_bSO_2$, wherein $R_b$ is $C_{1-10}$ alkyl;
or $R_2$ and $R_3$ together with a carbon atom to which they are bonded to represent a carbonyl group; and
X is halogen or sulfonyloxy.

2. A compound chosen from

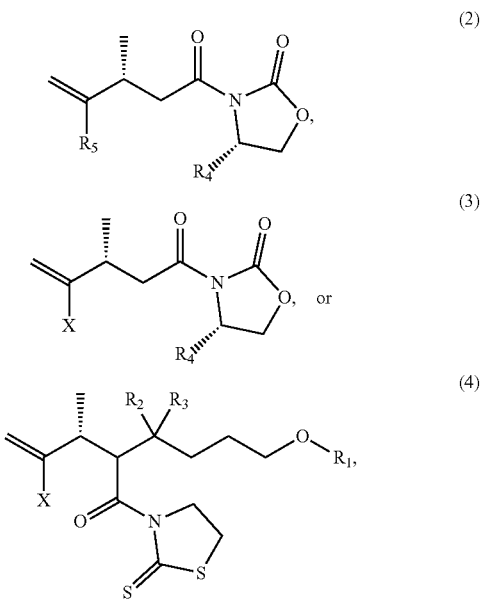

wherein, $R_1$ is a hydroxyl protecting group;
$R_2$ and $R_3$ are the same or different, and independently selected from H and $OR_a$, and $R_a$ is independently selected from the group consisting of H, $C_{1-10}$ alkyl, and $R_bSO_2$, wherein $R_b$ is $C_{1-10}$ alkyl;
or $R_2$ and $R_3$ together with a carbon atom to which they are bonded represents a carbonyl group;
X is halogen or sulfonyloxy; and $R_4$ is $C_{1-10}$ alkyl, substituted or unsubstituted phenyl, or substituted or unsubstituted benzyl, and $R_5$ is a silyl group.

3. A method for preparing halichondrins, eribulin, pharmaceutically acceptable salts thereof or C20-C26 fragment thereof, comprising hydrolyzing the compound of Formula (7) in the solvent to obtain the compound of Formula (8) according to claim 1.

4. The method for preparing the compound of Formula (8) of claim 1, further comprising oxidizing a compound of Formula (6) to form the compound of Formula (7) in which $R_2$ and $R_3$ together with the carbon atom to which they are bonded represent a carbonyl group:

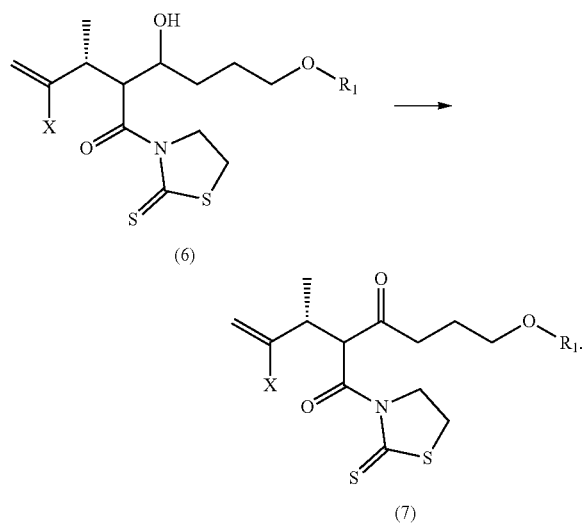

5. The method for preparing the compound of Formula (8) of claim 1, further comprising preparing the compound of Formula (7), wherein $R_2$ is H and $R_3$ is OH, from a compound of Formula (5) and O=CH—(CH$_2$)$_3$—O—$R_1$:

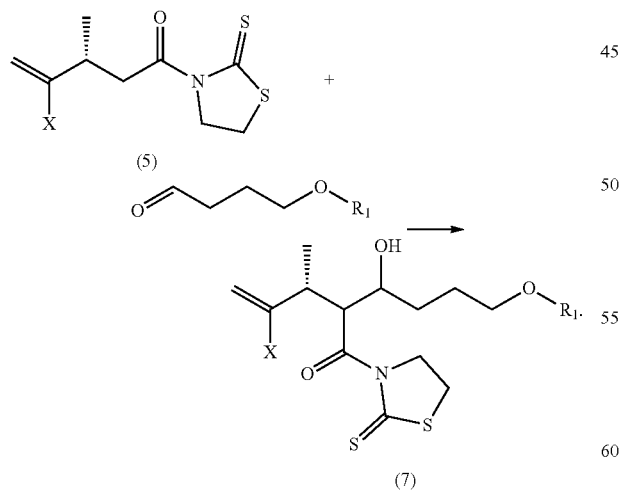

6. The method for preparing the compound of Formula (8) of claim 5, further comprising the step of preparing the compound of Formula (5) by coupling a compound of Formula (4) and thiazoline-2-thione:

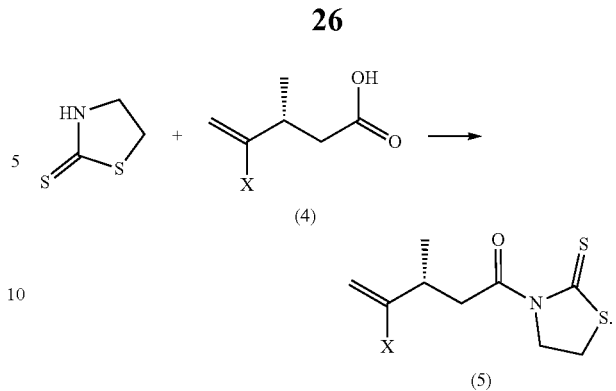

7. The method for preparing the compound of Formula (8) of claim 6, further comprising the step of preparing the compound of Formula (4) by hydrolyzing a compound of Formula (3):

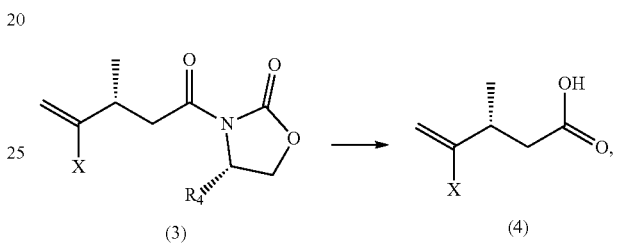

wherein, $R_4$ is $C_{1-10}$ alkyl, substituted or unsubstituted phenyl, or substituted or unsubstituted benzyl.

8. The method for preparing the compound of Formula (8) of claim 7, further comprising the step of preparing the compound of Formula (3) from a compound of Formula (2) in presence of a halogenation reagent containing X, wherein X is halogen:

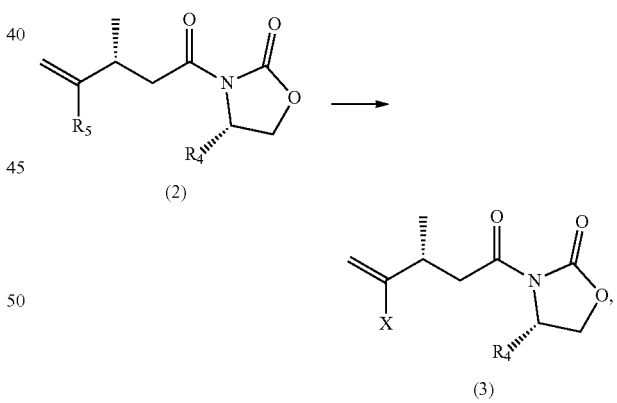

wherein, $R_5$ is a silyl group.

9. The method for preparing the compound of Formula (8) of claim 8, further comprising the step of reacting a compound of Formula (1) with a Grignard reagent $R_6$MgX or $R_6$Li, wherein $R_6$ is

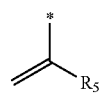

and X is halogen, to obtain the compound of Formula (2):

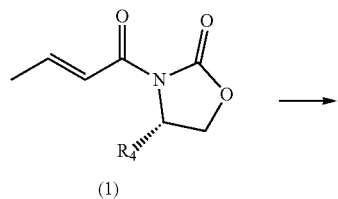

(1)

10. The method for preparing the compound of Formula (8) of claim 9, further comprising the step of recrystallizing the compound of Formula (2) once, twice, or more times.

11. The method for preparing the compound of Formula (8) of claim 10, further comprising the step of preparing the compound of Formula (1) from an oxazolidinone chiral auxiliary (S)-(−)-4-$R_4$-2-oxazolidinone and an acyl compound, the acyl compound being an ester, a carboxylic acid, an acyl halide, or an acid anhydride:

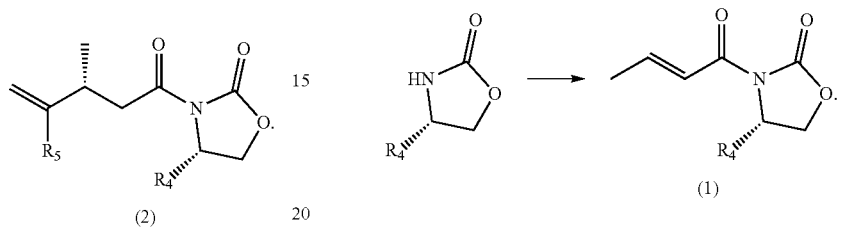

(2)

* * * * *